US005565576A

United States Patent [19]

Hall et al.

[11] Patent Number: 5,565,576
[45] Date of Patent: Oct. 15, 1996

[54] HALOHYDANTOIN AND FATTY AMIDE COMPOSITION FOR COMPACTION, PROCESS OF COMPACTING AND PRODUCT PRODUCED THEREBY

[75] Inventors: Larry K. Hall, Nazareth, Pa.; Julia A. Falter, Glen Gardner; Thomas E. Farina, Flemington, both of N.J.

[73] Assignee: Lonza Inc., Fair Lawn, N.J.

[21] Appl. No.: 330,251

[22] Filed: Oct. 27, 1994

[51] Int. Cl.$^6$ .......................... A61K 33/22; A61K 31/41; A01N 59/14; A01N 43/50; C07D 233/72

[52] U.S. Cl. .......................... 548/317.1; 424/464; 510/192; 510/382

[58] Field of Search .................. 548/317.1; 514/389, 514/390, 960; 424/464

[56] References Cited

U.S. PATENT DOCUMENTS

| | | | |
|---|---|---|---|
| 3,345,371 | 10/1967 | Paterson | 548/317.1 |
| 3,412,021 | 11/1968 | Paterson | 210/62 |
| 4,242,216 | 12/1980 | Daugherty et al. | 252/103 |
| 4,532,330 | 7/1985 | Cole | 548/311 |
| 4,621,096 | 11/1986 | Cole | 514/389 |
| 4,677,130 | 6/1987 | Puzig | 514/389 |
| 4,728,453 | 3/1988 | Choy | 252/91 |
| 5,057,612 | 10/1991 | Worley et al. | 548/317.1 X |
| 5,149,541 | 9/1992 | Leis, Jr. et al. | 424/489 |
| 5,256,328 | 10/1993 | Cavanagh et al. | 252/102 |

FOREIGN PATENT DOCUMENTS

| | | | |
|---|---|---|---|
| 0627194 | 9/1961 | Canada | 548/317.1 |
| 0704163 | 2/1965 | Canada | 548/317.1 |
| 1230825 | 12/1987 | Canada | A10N 43/50 |
| 0868876 | 5/1961 | United Kingdom | 548/317.1 |
| 0915909 | 1/1963 | United Kingdom | 548/317.1 |
| 0928897 | 6/1963 | United Kingdom | 548/317.1 |

*Primary Examiner*—Floyd D. Higel
*Attorney, Agent, or Firm*—Darby & Darby, P.C.

[57] ABSTRACT

N-halohydantoins are advantageously compacted with saturated, normally solid, fatty amides.

23 Claims, 2 Drawing Sheets

HALOHYDANTOIN AND FATTY AMIDE COMPOSITION FOR COMPACTION, PROCESS OF COMPACTING AND PRODUCT PRODUCED THEREBY

BACKGROUND OF THE INVENTION

N-halohydantoin compounds are used commercially in industrial and recreational water treatment to provide biocidal action and to control bacterial growth. Recently, these compounds have also been used in household automatic toilet bowl cleaners. Examples of N-halohydantoins currently being used in these applications include N,N'-dichloro- and N,N'-dibromo- derivatives, as well as mixtures of N,N'-chloro and -bromo derivatives.

N-halohydantoin compounds are typically produced as solid particulates. They are often compacted by mechanical pressure into forms such as briquettes, tablets and pucks. These "compacts" are normally subjected to various stresses and shocks during packaging, transport and end-use. Because of this, it is highly desirable to have a composition for compaction that not only molds easily, but better withstands stresses and shocks.

Various binders have been used in the compaction process. Most organic materials, however, cannot be used as binders with N-halohydantoins because of the N-halohydantoins' strong oxidizing properties. Severe reactivity with the N-halohydantoins results in substantial discoloration of the finished product.

U.S. Pat. No. 3,412,021 teaches using polymers as binders, with copious amounts of water, to form 1-bromo-3-chloro-5,5-dimethylhydantoin into sticks or rods. A paste is made that consists of at least 25% water. However, excess water renders the polymers inactive, thereby preventing curing. The resulting compacts are not acceptable. In addition, compacts formed by this process are not as hard as is desirable, unless a post-application drying process is performed. The cost of evaporating water to make an acceptable product is prohibitive.

U.S. Pat. No. 4,677,130 describes adding dry, particulate alkali metal or alkaline earth metal salts to N-halohydantoins, and then compacting. While this process does not require water (as in U.S. Pat. No. 3,412,021), use of alkali earth metal salts has several drawbacks. For example, while the compact formed, e.g., using magnesium stearate, is thermally stable, it has a lower decomposition temperature (as measured by differential scanning calorimetry). This is caused by the reaction between the N-halohydantoin and the alkali earth metal salt. Off-color products result where ambient temperature is not sufficiently controlled. Nor is it possible to modify the rate of dissolution of the N-halohydantoin using alkali salts. Modifying the rate of dissolution is desirable, for example, to extend the functional lives of toilet bowl cleaners and urinal tablets.

Canadian patent 1,230,825 describes the use of borax (e.g. $Na_2B_4O_7 \cdot 5H_2O$) as a binder for N-halogenated hydantoins. Adding borax produces tablets that are essentially dust-free, have a high minimum break strength, and have dissolution characteristics that can be modified by varying the amount of borax. However, the patent indicates that a separate additive, such as stearic acid or sodium stearate, is required to lubricate die surfaces. Such additives melt at low temperature (e.g. 55°–65° C.), resulting in a markedly lower decomposition temperature for the compacted products.

SUMMARY OF THE INVENTION

It has now been found that saturated, normally solid, fatty amides are fully compatible with N-halohydantoins for forming compacted products, while at the same time lubricating die and processing surfaces. The fatty amides also increase the resistance to crumbling and decrease the dissolution rate of the compacted product. In one embodiment, the invention relates to a composition for compaction comprising an N-halohydantoin and an effective amount of a saturated, normally solid, fatty amide binder. In another embodiment, the invention relates to a method for forming compacted N-halohydantoin wherein the N-halohydantoin is mixed with the fatty amide, and then compressed to form a compacted product. In another embodiment, the invention relates to the compacted product of N-halohydantoin and fatty amide.

DETAILED DESCRIPTION OF THE INVENTION

Figure 1:
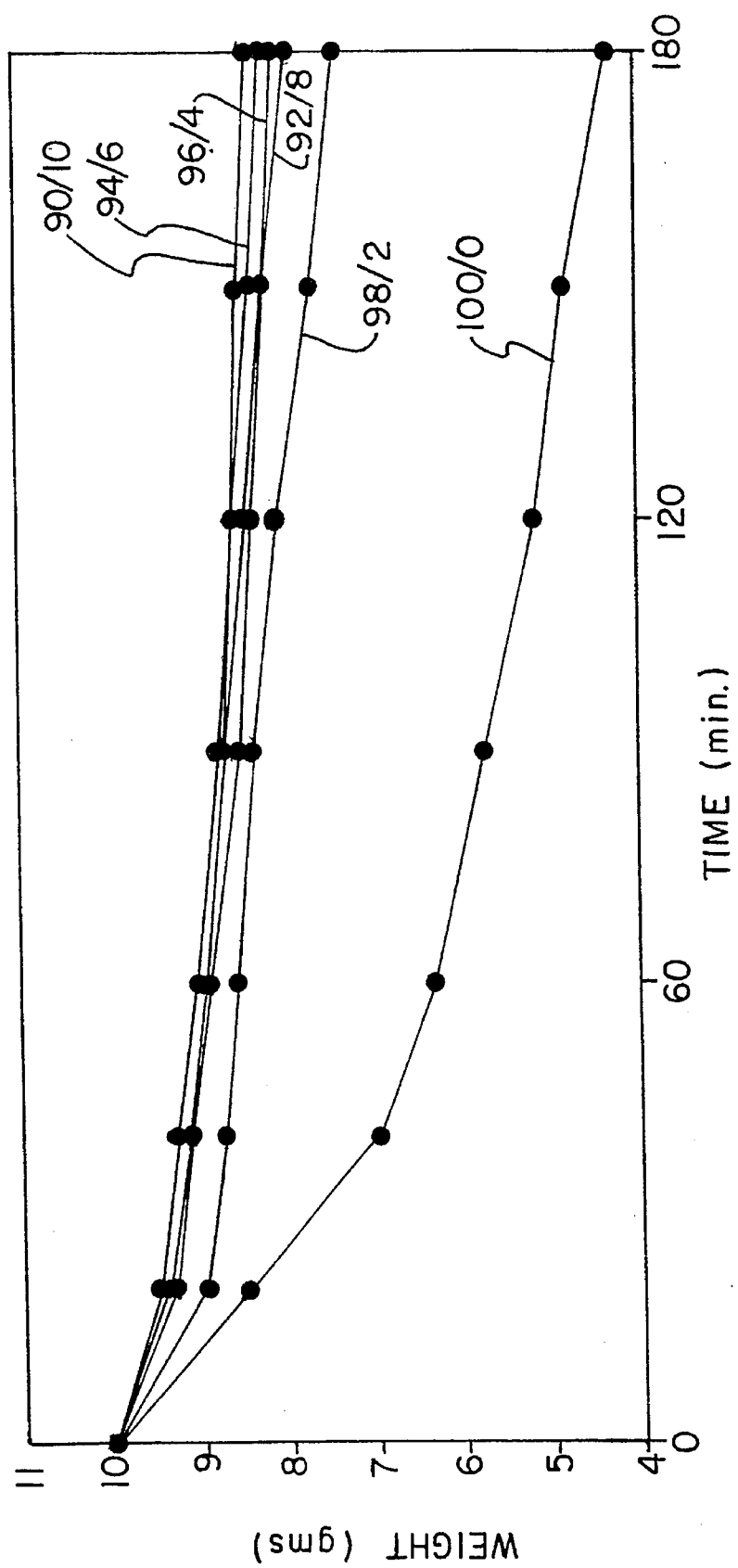
FIG. 1 is a graph of tablet friability for tablets containing different ratios of N-halohydantoin to fatty amide.

Saturated, normally solid, fatty amide waxes can be used to compact halohydantoins to provide stable final forms. Conventional compacted forms, including tablets, briquettes and pucks, can be made using this invention. The word "compacted," however, is also intended to encompass any other products that result from the compression of N-halohydantoins, such as, granules, sticks, and other agglomerates. "Normally solid" refers to fatty amides that are solid at room temperature.

The compacted forms according to the invention show markedly increased resistance to crumbling and breakage. Additionally, they show better thermal stability than those made with, for example, alkaline earth metal salts such as magnesium stearate (a conventional binder/lubricant used in N-halohydantoin forming operations).

N-halohydantoin compounds of the formula shown can be used in this invention.

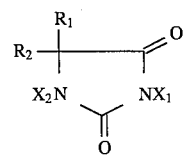

$R_1$ and $R_2$ are independently selected from alkyl groups (having from 1 to 12 carbons), and $X_1$ and $X_2$ are independently selected from bromine, chlorine and hydrogen, at least one of $X_1$ and $X_2$ being halogen. In preferred embodiments, $R_1$ is methyl and $R_2$ is either methyl or ethyl. Preferred halohydantoins include 1,3-dichloro-5,5-dimethylhydantoin; 1,3-dibromo-5,5-dimethylhydantoin; and combinations of these derivatives. Another preferred embodiment includes a mixture of halogen derivatives of 5-methyl-5-ethylhydantoin, such as, the mixtures currently sold under the tradenames Dantobrom® RW and Dantochlor®.

Examples of saturated, normally solid, fatty amides which may be combined with N-halohydantoins include primary fatty amides having from 6 to 22 carbons, such as stearamide, palmitamide, caprylamide, lauramide, and behenamide, and secondary fatty amides. Preferred are secondary fatty amides that are the reaction products of ethylenediamine and fatty acids containing from 6 to 22 carbons. Most preferred of this type are ethylenebisstearamide (EBS), and ethylenebisisostearamide. Ethylenebisamides can be synthesized from a variety of fatty acids and ethylenediamine. All have exceptionally high melting points for organic waxes and, interestingly, increase in melting point with decreasing molecular weight. As shown by the examples in Table 1, melting points increase from 124° C. for ethylene [N-stearamide, N'-cyclohexyl(methoxamide)] to a high of 166° C. for ethylene biscaprylamide.

TABLE 1

| ETHYLENE BISAMIDE | MELTING RANGE (°C.) |
|---|---|
| Ethylene biscaprylamide | 166–168 |
| Ethylene bispelargamide | 159–165 |
| Ethylene bislauramide | 154–159 |
| Ethylene [N-stearamide, N'-benzoamide] | 154 |
| Ethylene bispalmitamide | 147–150 |
| Ethylene bisstearamide | 140–145 |
| Ethylene bisbehenamide | 139 |
| Ethylene [N-stearamide, N'-cyclohexyl(methoxamide)] | 124 |

Even small amounts of fatty amide have been found to provide significant benefits, such as increased hardness of the compacted product, increased stability, and lubrication during compaction. The amount of fatty amide is preferably from about 0.1% to about 25% by weight. In a preferred embodiment, the amount of fatty amide is about 10% by weight.

The fatty amide may be conventionally mixed with the N-halohydantoin using a commercially available mixer. Examples of such mixers are a V cone blender (Paterson-Kelley), a "Henschel" type mixer, a ball mill, and a rotary cone tumbler.

If desired, other additives may be employed, including inorganic salts such as borate and calcium chloride. To compact the blended mixture, conventional equipment, such as a briquettor, pelletizor, granulator (Chilsinator), punch press, "Carver" type press, "Bepex" type compactor, or rotary tablet press, may be used. In some cases, a pre-compaction step to produce a granular product may be employed. For example, corrugated sheets may be formed, and then broken up to form granules. Also, if desired, the compacted product may be broken into a specific screen size and used for subsequent compaction.

The following Examples are intended to illustrate the invention, but in no way limit its scope.

EXAMPLE 1

1,3-dichloro-5,5-dimethylhydantoin/1,3-dichloro-5-ethyl-5-methylhydantoin (DCDMH/DCEMH) (Dantochlor®), and a mixed bromo-chloro hydantoin derivative (MBCH) (Dantobrom RW®) were blended with ethylenebisstearamide (EBS). Blends were prepared by hand mixing until a homogeneous powder was obtained. Compaction was performed using a Carver press. Tablets were prepared in one inch dyes by compacting for 5 seconds at 20,000 pounds pressure. The samples and the storage temperatures are set forth below:

TABLE 2

| SAMPLE | TEMP. | OBSERVATION |
|---|---|---|
| 50% DCDMH/DCEMH 50% EBS | 26° C. | Hard White Tablet |
| Same | 50° C. | Hard White Tablet |
| 50% MBCH 50% EBS | 26° C. | Hard White Tablet |
| Same | 50° C. | Hard White Tablet |

In each case, after 1 month, the compacted mass remained as a hard white tablet. This demonstrates that there is no adverse reaction between the N-halohydantoin and EBS, even at temperatures considerably higher than those normally experienced in storage areas during the summer.

EXAMPLE 2

DCDMH/DCEMH and EBS were compacted to form 10 g tablets at the following ratios: 100:0; 98:2; 95:5; 90:10; 80:20; and 50:50. Each tablet was placed in a separate jar and then fastened to a rotary apparatus which tumbled the tablets for three hours. Samples were taken every twenty minutes for the first hour and hourly thereafter.

As shown in FIG. 1, tablet friability decreased in proportion to the weight of the EBS present. Interestingly, the addition of only 2% by weight of EBS reduced friability by 25%, as measured by the weight of tablet remaining vs. the weight lost to crumbling and fines. Even at this low level of additive, a significant increase in tablet integrity resulted. Additional gains in tablet integrity were made at elevated levels of EBS, up to the 50:50 DCDMH/DCEMH:EBS mixture.

EXAMPLE 3

Figure 2:
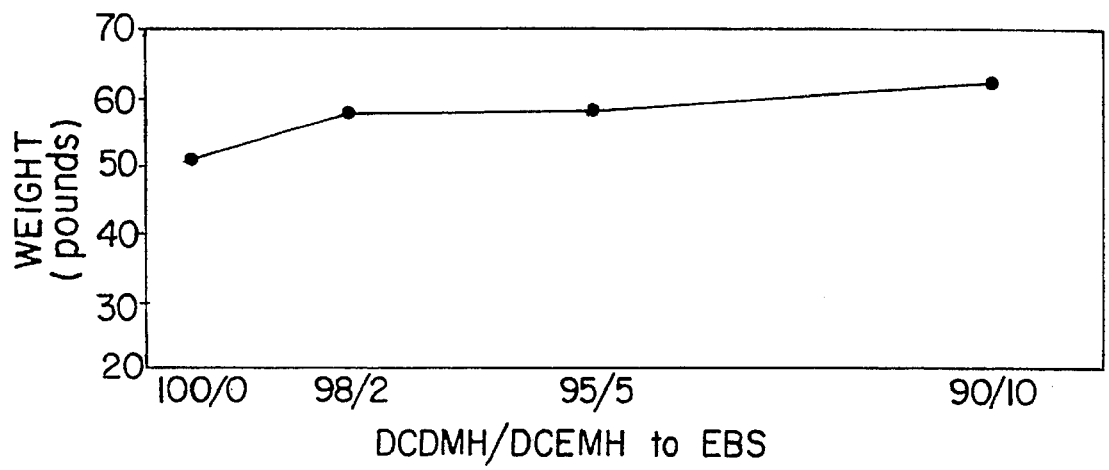
FIG. 2 is a graph of tablet hardness for tablets containing different ratios of N-halohydantoin to fatty amide.

Each tablet from Example 2 was evaluated for hardness using an Instron™ multipurpose tester. FIG. 2 indicates the relative hardness of each compact. As shown, tablet hardness increased dramatically with only small additions of EBS.

EXAMPLE 4

Tablets prepared with 95% DCDMH/DCEMH and 5% EBS were compared with tablets containing 95% DCDMH/DCEMH and 5% magnesium stearate, using differential scanning calorimetry (DSC). The DSC data were analyzed to determine the onset of decomposition and the exotherm heat. Results are shown in Table 3.

TABLE 3

| SAMPLE | DECOMPOSITION TEMP (°C.) | EXOTHERM (CAL/G) |
|---|---|---|
| MBCH | 182 | 75.6 |
| 95% MBCH 5% EBS | 167 | 175.2 |
| 95% MBCH 5% Magnesium Stearate | 142 | 220.0 |

These results demonstrate the improved inherent stability of N-halohydantoin tablets containing EBS compared to tablets containing magnesium stearate. As shown, MBCH itself decomposed at 182° C. When 5% magnesium stearate was used, the decomposition temperature was reduced to 142° C., whereas when 5% EBS was used the temperature was reduced only to 167° C. This shows that EBS is a more chemically stable additive to N-halohydantoins than magnesium stearate. In addition, when decomposition occurred, less exotherm was observed with EBS than with magnesium stearate. This also indicates superior stability of EBS.

Figure 3:
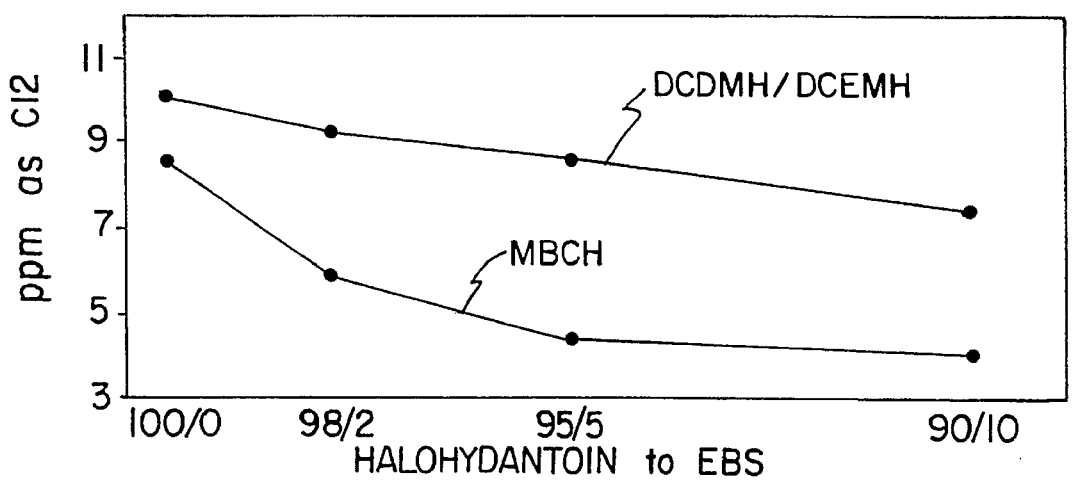
FIG. 3 is a graph showing the dissolution rate of N-halohydantoin tablets containing different ratios of N-halohydantoin to fatty amide.

The addition of EBS to halohydantoins was also found to decrease the dissolution rate of N-halohydantoin tablets (FIG. 3). As little as 2% EBS substantially lowered the dissolution rate of DCDMH/DCEMH and MBCH (measured in ppm total halogen).

EXAMPLE 5

The effect of various amounts of ethylenebisamide on tablet integrity, when combined with bromochloro-dimethylhydantoin (BCDMH), is shown in Table 4. The tablets were formed as described in Example 1.

TABLE 4

| BCDMH/EBS | Tablet appearance |
|---|---|
| 100/0 | Shattered, flaked tablet |
| 95/5 | Slight splitting |
| 90/10 | Good solid tablet |

As shown, the addition of 10% ethylenebisstearamide markedly improved tablet compaction and integrity, allowing BCDMH to be tabletted without the need for other additives or binders.

We claim:

1. A composition comprising an admixture of:

(A) at least one N-halohydantoin having the formula:

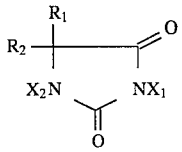

wherein $R_1$ and $R_2$ are independently selected from lower alkyl groups having from 1 to 12 carbon atoms, and wherein $X_1$ and $X_2$ are independently selected from the group consisting of bromine, chlorine and hydrogen, at least one of $X_1$ and $X_2$ being halogen; and (B) an amount of a saturated, normally solid, fatty amide effective to bind said composition.

2. The composition of claim 1 wherein $R_1$ is methyl and $R_2$ is methyl or ethyl.

3. The composition of claim 1 wherein said fatty amide is a primary fatty amide having from 6 to 22 carbon atoms.

4. The composition of claim 3 wherein said fatty amide is selected from the group consisting of stearamide, palmitamide, caprylamide, lauramide, and behenamide.

5. The composition of claim 1 wherein said fatty amide is a reaction product of ethylenediamine and a fatty acid having from 6 to 22 carbon atoms.

6. The composition of claim 5 wherein said fatty amide is selected from the group consisting of ethylenebisstearamide, ethylenebisisostearamide, ethylene biscaprylamide, ethylene bispelargamide, ethylene bislauramide, and ethylene bispalmitamide.

7. The composition of claim 6 wherein said fatty amide is ethylenebisstearamide.

8. The composition of claim 1 wherein said N-halohydantoin is selected from the group consisting of 1,3-dichloro-5, 5-dimethylhydantoin, 1,3-dibromo-5,5-dimethylhydantoin, and a halogen derivative of 5-methyl-5-ethylhydantoin.

9. The composition of claim 1 comprising two N-halohydantoins in admixture with said fatty amide.

10. A compacted N-halohydantoin product comprising:

(A) at least one N-halohydantoin having the formula

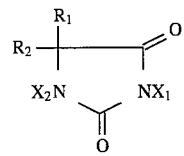

wherein $R_1$ and $R_2$ are independently selected from lower alkyl groups having 1 to 12 carbon atoms, and wherein $X_1$ and $X_2$ are independently selected from the group consisting of bromine, chlorine and hydrogen, at least one of $X_1$ and $X_2$ being halogen; and (B) an amount of a saturated, normally solid, fatty amide effective to bind said product.

11. The composition of claim 10 wherein $R_1$ is methyl and $R_2$ is methyl or ethyl.

12. The composition of claim 10 wherein said fatty amide is a primary fatty amide having from 6 to 22 carbon atoms.

13. The composition of claim 10 wherein said fatty amide is selected from the group consisting of stearamide, palmitamide, caprylamide, lauramide, and behenamide.

14. The composition of claim 10 wherein said fatty amide is a reaction product of ethylenediamine with a fatty acid having from 6 to 22 carbon atoms.

15. The composition of claim 14 wherein said fatty amide is selected from the group consisting of ethylenebisstearamide, ethylenebisisostearamide, ethylene biscaprylamide, ethylene bispelargamide, ethylene bislauramide, and ethylene bispalmitamide.

16. The composition of claim 15 wherein said fatty amide is ethylenebisstearamide.

17. The composition of claim 10 wherein said N-halohydantoin is selected from the group consisting of 1,3-dichloro-5,5-dimethylhydantoin, 1,3-dibromo-5,5-dimethylhydantoin, and a halogen derivative of 5-methyl-5-ethylhydantoin.

18. The composition of claim 17 wherein said N-halohydantoin is a halogen derivative of 5-methyl-5-ethylhydantoin.

19. The composition of claim 10 wherein said fatty amide is present in an amount between 0.1% and 25% by weight of said composition.

20. The composition of claim 10 wherein the fatty amide is present in an amount equal to about 10% by weight of said composition.

21. In a process for compacting an N-halohydantoin, wherein said N-halohydantoin is admixed with a binder and compressed to form a compacted product, the improvement comprising using a saturated, normally solid, fatty amide as the binder.

22. The composition of claim 10 wherein said compacted N-halohydantoin product is a tablet, a briquette, or a puck.

23. The composition of claim 10 that results from compaction at a pressure of about 2000 lbs.

* * * * *